United States Patent [19]
Gustafsson et al.

[11] Patent Number: 6,153,428
[45] Date of Patent: *Nov. 28, 2000

[54] α(1,3) GALACTOSYLTRANSFERASE NEGATIVE PORCINE CELLS

[75] Inventors: Kenth T. Gustafsson, Amersham, United Kingdom; David H. Sachs, Newton, Mass.

[73] Assignee: BioTransplant, Inc., Charlestown, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/621,700

[22] Filed: Mar. 26, 1996

Related U.S. Application Data

[63] Continuation of application No. 08/228,933, Apr. 13, 1994, abandoned.

[51] Int. Cl.[7] .............................. C12N 5/00; C12N 15/00; A61K 48/00
[52] U.S. Cl. .................... 435/325; 435/320.1; 424/93.21
[58] Field of Search ................................ 800/2; 424/93.1, 424/93.21; 435/320.1, 325

[56] References Cited

U.S. PATENT DOCUMENTS 5,821,117  10/1998  Sandrin et al. .

OTHER PUBLICATIONS

Pursel et al., J. Reprod. Fert. Suppl. 40: 235–245 (1990).
Dabkowski et al., Transplantation Proceedings 25(5): 2921 (1993).
Sandrin et al., PNAS 90: 11391–11395 (1993).
Toziasse et al., J Biol. Chem. 264(24): 14290–14297.
Larsen et al., PNAS 86: 8227—8231 (1989).
Cohen, Pharmac. Ther. 52: 211–255 (1991).
Wickstrom et al., FASEB J 5(5): A1443 (1991).
Long et al., FASEB J. 7(1): 25–30 (1993).
Ramirez–Solis et al., Meth. Enzymology 225 :855–878 (1993).
Stein et al., Science 261: 1004–1012 (1993).
Cairns, et al., "Xeongrafts—future prospects for clinical transplantation," *Immunology Letters*, 29:167–170 (1991).
Kirkman, R.L., "Of swine and men: organ physiology in different species," *Xenograft*, 25:125–132 (1989).
Pepin, et al., "Impaired type II glucocorticoid–receptor function in mice bearing antisense RNA transgene," *Nature*, 355:725–728 (1992).
Pouncey, et al., "β 1–4–Galactosyltransferase Gene Expression is Regulated During Entry into the Cell Cycle and During the Cell Cycle," *Somatic Cell And Molecular Genetics*, 17(5):435–443 (1991).
Pursel, et al., "Expression and performance in transgenic pigs," *Journal of Reproduction and Fertility*, Supplement, 40:235–245 (1990).
Strahan, et al., "Pig α 1, 3Galactosyltransferase: Sequence of a Full–Length cDNA Clone, Chromosomal Localisation of the Corresponding Gene, and Inhibition of Expression in Cultured Pig Endothelial Cells," *Transplantation Proceedings*, 27(1):245–246 (1995).
Uhlmann, E and Peyman, A., "Antisense oligonucleotides: A new therapeutic principle," *Chemical Reviews*, 90(4):543–584 (1990).
Vanhove et al. (1998) Annals N.Y. Acad. Sci. 862, 28–36.
Bradley et al. (1992) Bio/Technol. 10, 534–539.
Shim et al. (1997) Biol. Reprod. 57, 1089–1095.
Hayashi et al (1997) Transplantation Proced. 29, 893.
Strahan et al (1995) Transplantation Proced. 27, 245.
Strahan et al (1995) Xenotransplantation 2, 143–147.
Mullins et al (1996) Journal of Clinical Investigation 98, p. S37–S40.
Seamark (1994) Reproductive Fertility and Development 6, 653–657.
Mullins et al (1993) Hypertension 22, 630–633.
Sokol et al (1996) Transgenic Res. 5, 363–371.
James (1991) Antiviral Chem. & Chemother. 2, 191–214.
Wickstrom et al (1991) FASEB J. 5, A1443.
Dabkowski et al (1993) Transplant. Proced. 25, 2921.
Pursel et al (1990) J. Reprod. Fert. Suppl. 40, 235–245.

*Primary Examiner*—Deborah Crouch
*Attorney, Agent, or Firm*—E. M. Olstein; R. J. Lillie

[57] ABSTRACT

Transgenic swine in which the normal expression of α(1,3) galactosyltransferase is prevented in at least one organ of tissue type. The absence or inactivation of this enzyme prevents the production of carbohydrate moieties having the distinctive terminal Galα1-3Galβ1-4GlcNAc epitope that is a significant factor in xenogeneic, particularly human, transplant rejection of swine grafts.

5 Claims, 5 Drawing Sheets

FIG. 1A

```
5'-CATGAGGAGA AAATA ATG AAT GTC AAA GGA AGA GTG GTT CTG TCA ATG
CTG CTT GTC TCA ACT GTA ATG GTT TGG GAA TAC ATC AAC AGC
CCA GAA GGT TCT TTG TTC TGG ATA TAC CAG TCA AAA AAC CCA GAA GTT
GGC AGT GCT CAG AGG GGC TGG TTT CCG AGC TGG TTT AAC AAT
GGG ACT CAC AGT TAC CAC GAA GAA GAC GCT ATA GGC AAC GAA AAG
GAA CAA AGA AAA GAC AAC AGA GGA GAG CTT CCG CTA GTG GAC TGG
TTT AAT CCT GAG AAA CGC CCA GAG GTC GTG ACC ATA ACC AGA TGG AAG
GCT CCA GTG GTA TGG GAA GGC ACT TAC AAC AGA GCC GTC TTA GAT AAT
TAT TAT GCC AAA CAG AAA ATT ACC GTG GGC TTG ACG GTT TTT GCT GTC
GGA AGA TAC ATT GAG CAT TAC TTG GAG GAG TTC TTA ATA TCT GCA AAT
ACA TAC TTC ATG GTT GGC CAC AAA GTC ATC TTT TAC ATC ATG GTG GAT
GAT ATC TCC AGG ATG CCT TTG ATA GAG CTG GGT CCT CTG CGT TCC TTT
AAA GTG TTT GAG ATC AAG TCC GAG AAG AGG TGG CAA GAC ATC AGC ATG
ATG CGC ATG AAG ACC ATC GGG GAG GAG CAC ATC CTG GCC CAC ATC CAG CAC
```

FIG. 1B

```
GAG GTG GAC TTC CTC TTC TGC ATG GAC GTG GAT CAG GTC TTC CAA AAC
AAC TTT GGG GTG GAG ACC CTG GGC CAG TCG GTG GCT CAG CTA CAG GCC
TGG TGG TAC AAG GCA CAT CCT GAC GAG TTC ACC TAC GAG AGG CGG AAG
GAG TCC GCA GCC TAC ATT CCG TTT GGC CAG GGG GAT TTT TAT TAC CAC
GCA GCC ATT TTT GGG GGA ACA CCC ACT CAG GTT CTA AAC ATC ACT CAG
GAG TGC TTC AAG GGA ATC CTC CAG GAC AAG GAA AAT GAC ATA GAA GCC
GAG TGG CAT GAT GAA AGC CAT CTA AAC AAG TAT TTC CTT CTC AAC AAA
CCC ACT AAA ATC TTA TCC CCA GAA TAC TGC TGG GAT TAT CAT ATA GGC
ATG TCT GTG GAT ATT AGG ATT GTC AAG ATA GCT TGG CAG AAA AAA GAG
TAT AAT TTG GTT AGA AAT AAC ATC TGA CTTTAAATTG TGCCAGCAGT
TTTCTGAATT TGAAAGAGTA TTACTCTGGC TACTTCCTCA GAGAAGTAGC ACTTAATTTT
AACTTTTAAA AAAATACTAA CAAAATACCA ACACAGTAAG TACATATTAT TCTTCCTT -
3'
```

FIG. 2A

| | | | | | |
|---|---|---|---|---|---|
| Porcine | MNVKGRVVLS | MLLVSTVMVV | FWEYINSPEG | SLFWIYQSKN | PEV-GSSAQR | 49 |
| Bovine  | MNVKGKVILS | MLVVSTVIVV | FWEYIHSPEG | SLFWINPSRN | PEVGGSSIQK | 50 |
| Murine  | MNVKGKVILL | MLIVSTVVVV | FWEYVNSPDG | SFLWIYHTKI | PEVGENRWQK | 50 |

| | | | | | |
|---|---|---|---|---|---|
| Porcine | GWWFPSWFNN | GTHSYHEEED | AIGNEKEQRK | EDNRGELPLV | DWFNPEKRPE | 99 |
| Bovine  | GWWLPRWFNN | GYH---EEDG | DINEEKEQRN | EDESK-LKLS | DWFNPFKRPE | 96 |
| Murine  | DWWFPSWFKN | GTHSYQ-EDN | VEGRREKGRN | GDRIEEPQLW | DWFNPKNRPD | 99 |

| | | | | | |
|---|---|---|---|---|---|
| Porcine | VVTITRWKAP | VVWEGTYNRA | VLDNYYAKQK | ITVGLTVFAV | GRYIEHYLEE | 149 |
| Bovine  | VVTMTKWKAP | VVWEGTYNRA | VLDNYYAKQK | ITVGLTVFAV | GRYIEHYLEE | 146 |
| Murine  | VLTVTPWKAP | IVWEGTYDTA | LLEKYYATQK | LTVGLTVFAV | GKYIEHYLED | 149 |

| | | | | | |
|---|---|---|---|---|---|
| Porcine | FLISANTYFM | VGHKVIFYIM | VDDISRMPLI | ELGPLRSFKV | FEIKSEKRWQ | 199 |
| Bovine  | FLTSANKHFM | VGHPVIFYIM | VDDVSRMPLI | ELGPLRSFKV | FKIKPEKRWQ | 196 |
| Murine  | FLESADMYFM | VGHRVIFYVM | IDDTSRMPVV | HLNPLHSLQV | FEIRSEKRWQ | 199 |

FIG. 2B

| | | | | | |
|---|---|---|---|---|---|
| Porcine | DISMMRMKTI | GEHILAHIQH | EVDFLFCMDV | DQVFQNNFGV | ETLGQSVAQL | 249 |
| Bovine | DISMMRMKTI | GEHIVAHIQH | EVDFLFCMDV | DQVFQDKFGV | ETLGESVAQL | 246 |
| Murine | DISMMRMKTI | GEHILAHIQH | EVDFLFCMDV | DQVFQDNFGV | ETLGQLVAQL | 249 |

| | | | | | |
|---|---|---|---|---|---|
| Porcine | QAWWYKAHPD | EFTYERRKES | AAYIPFGQGD | FYYHAAIFGG | TPTQVLNITQ | 299 |
| Bovine | QAWWYKADPN | DFTYERRKES | AAYIPFGEGD | FYYHAAIFGG | TPTQVLNITQ | 296 |
| Murine | QAWWYKASPE | KFTYERRELS | AAYIPFGEGD | FYYHAAIFGG | TPTHILNLTR | 299 |

| | | | | | |
|---|---|---|---|---|---|
| Porcine | ECFKGILQDK | ENDIEAEWHD | ESHLNKYFLL | NKPTKILSPE | YCWDYHIGMS | 349 |
| Bovine | ECFKGILKDK | KNDIEAQWHD | ESHLNKYFLL | NKPTKILSPE | YCWDYHIGLP | 346 |
| Murine | ECFKGILQDK | KHDIEAQWHD | ESHLNKYFLF | NKPTKILSPE | YCWDYQIGLP | 349 |

| | | | |
|---|---|---|---|
| Porcine | VDIRIVKIAW | QKKEYNLVRN | NI | 371 |
| Bovine | ADIKLVKMSW | QTKEYNVVRN | NV | 368 |
| Murine | SDIKSVKVAW | QTKEYNLVRN | NV | 371 |

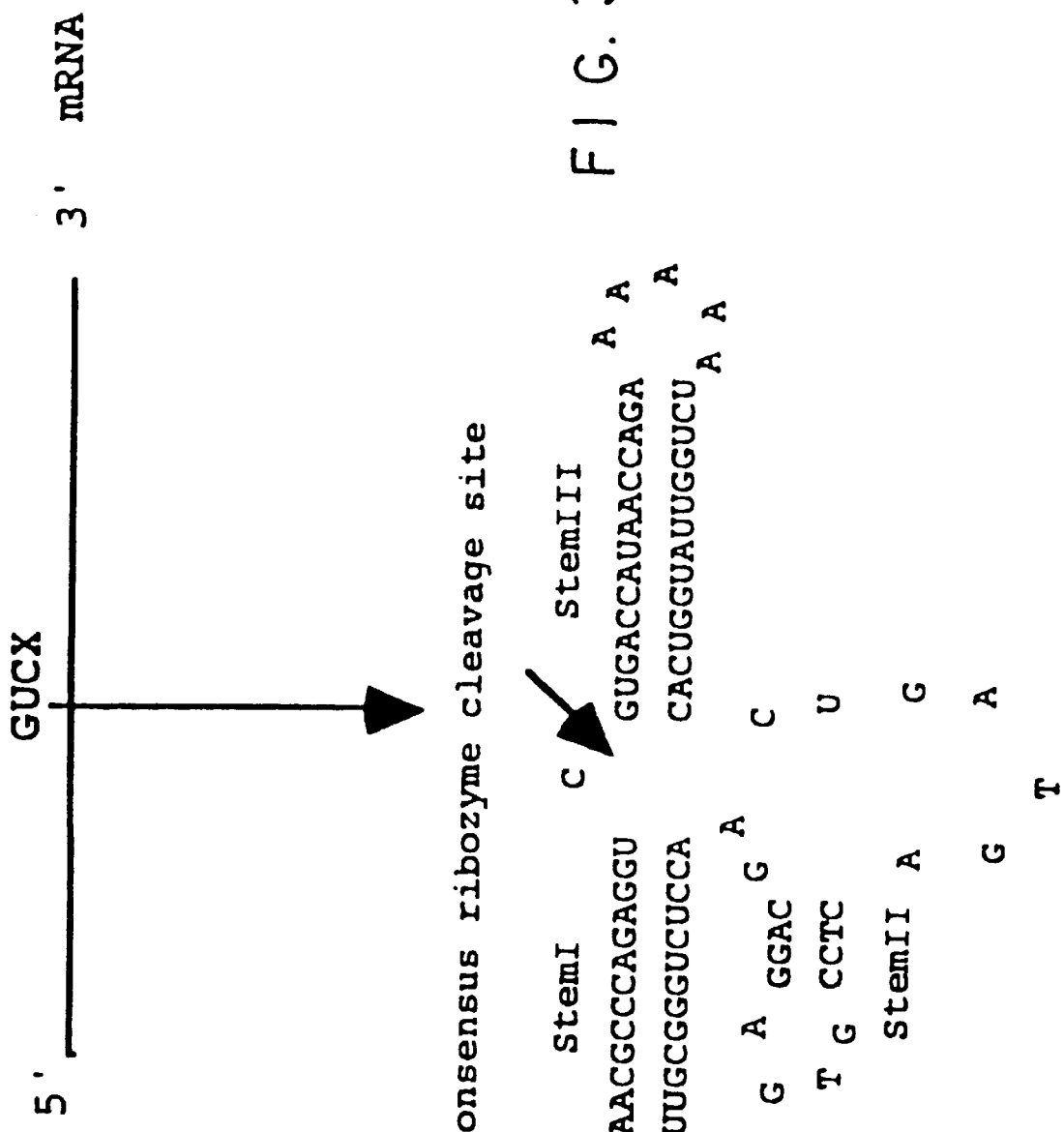

α(1,3) GALACTOSYLTRANSFERASE NEGATIVE PORCINE CELLS

This application is a continuation of application Ser. No. 08/228,933, filed Apr. 13, 1994 abandoned.

Donor organ shortages have led to hopes that xenotransplantation could serve as an alternative means of organ availability. Swine, particularly mini-swine, are an attractive alternative to non-human primate donors because of potentially greater availability, the reduced risk of zoonotic infections, appropriate size of organs and the reduced social and ethical concerns (Sachs, D. H. et al. 1976. Transplantation 22:559–567; Auchincloss, H. Jr. 1988. Transplantation 46:1–20). However, one of the major barriers to xenotransplantation is the phenomenon described as hyperacute rejection (Busch et al. 1972. Am. J. Pathology 79:31–57; Auchincloss, H. Jr. 1988. Transplantation 46:1–20). This phenomenon describes a very rapid and severe humoral rejection, which leads to destruction of the graft within minutes or hours of the transplant of the donor organ. Hyperacute rejection is apparently mediated by a complex series of events, including activation of the complement systems, activation of blood coagulation proteins, activation of endothelial cells and release of inflammatory proteins (Busch et al. 1972. Am. J. Pathology 79:31–57; Platt, J. L. 1992. ASAIO Journal 38:8–16). There is an accumulating body of information that implicates a group of pre-formed antibodies, the so-called natural antibodies, to be of fundamental importance in the hyperacute rejection seen in grafts between species. Species combinations in which the recipients of grafts have circulating antibodies that can initiate the hyperacute response to the donor species are described as discordant. Pigs and humans are one such discordant species combination.

The hyperacute rejection process is initiated when the natural antibodies of the recipient bind to cells of the donor organ (Platt et al. 1990. Transplantation 50:870–822; Platt et al. 1990. Immunology Today 11:450–456). It has been suggested that porcine N-linked carbohydrates carrying a terminal Galα1-3Galβ1-4GlcNAc structure are the major targets for anti-swine xenoreactive human natural antibodies (Good et al. 1992. Transplantation Proceedings 24:559–562; Sandrin et al. 1993. Proc. Natl. Acad. Sci. USA 90:11391–11395). One major difference between the glycosylation pattern of swine tissues and human tissues is the presence of high levels of a terminal Galα1-3Galβ1-4GlcNAc structure on swine cells and tissues. This structure is expressed at high levels in all lower mammals investigated, but is poorly expressed on cells and tissues of Old World monkeys, apes and humans (catarrhines) (Galili, U. and Swanson, K. 1992. Proc. Natl. Acad. Sci. USA 88:7401–7404; Galili et al. 1987. Proc. Natl. Acad. Sci. USA. 84:1369–1373). A specific transferase, UDP-Gal:Galβ1→4GlcNAc α1→3-galactosyltransferase (EC 2.4.1.151; α(1,3) galactosyltransferase) is responsible for the transfer of a terminal galactose to the terminal galactose residue of N-acetyllactosamine-type carbohydrate chains and lactosaminoglycans according to the reaction:

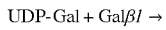

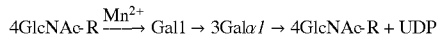

where R may be a glycoprotein or a glycolipid (Blanken, W. M. and Van den Eijinden, D. H. 1985. J. Biol. Chem. 260:12927–12934). Thus the Galα1-3Galβ1-4GlcNAc epitope. Full length cDNA sequences encoding the murine (Larsen et al. 1989. Proc. Natl. Acad. Sci. USA. 86:8227–8231) and bovine (Joziasse et al. 1989. J. Biol. Chem. 264:14290–14297) enzymes have been determined. In addition, the genomic organization of the murine a(1,3) galactosyltransferase gene has been established (Joziasse et al. 1992. J. Biol. Chem. 267:5534–5541). A partial sequence encoding the 3' region of the porcine α(1,3) galactosyltransferase cDNA gene has been determined (Dabkowski et al. 1993. Transplantation Proceedings. 25:2921) but the full length sequence has not been reported. The absence of the 5' sequence is significant for the applications described herein. In contrast to the lower mammals, humans do not express the α(1,3) galactosyltransferase. Furthermore, human sequences homologous to the murine sequence correspond to a processed pseudogene on chromosome 12 and an inactivated remnant on chromosome 9 (Shaper et al. 1992. Genomics 12:613–615).

In accordance with the invention, swine organs or tissues or cells that do not express α(1,3) galactosyltransferase will not produce carbohydrate moieties containing the distinctive terminal Galα1-3Galβ1-4GlcNAc epitope that is a significant factor in xenogeneic, particularly human, transplant rejection of swine grafts. Further in accordance with the invention, is the aspect of diminishing the production of α(1,3) galactosyltransferase to an extent sufficient to prevent the amount produced from providing carbohydrates with the Galα1-3Galβ1-4GlcNAc epitope from being presented to the cell surface thereby rendering the transgenic animal, organ, tissue, cell or cell culture immunogenically tolerable to the intended recipient without requiring complete α(1,3) galactosyltransferase gene suppression.

One principal aspect of the present invention is that the inventors have isolated the entire porcine α(1,3) galactosyltransferase cDNA gene (SEQ. ID NO. 1). The identification, isolation and sequencing of the entire cDNA gene, now particularly providing the sequence of the 5' end is an important advance because, as described in Example 2, this region has been identified as the most efficient for antisense targeting. Moreover, as compared with mouse and bovine homologous sequences (FIG. 2), this region of the α(1,3) galactosyltransferase mRNA appears to deviate extensively between these species making it extremely unlikely that a use of "cross-species" antisense constructs would be successful.

Another principle aspect of this invention related to genetically altered animals, more specifically transgenic, chimeric or mosaic swine in which the expression of biologically active α(1,3) galactosyltransferase is prevented in at least one organ, tissue or cell type. Transgenic animals carry a gene which has been introduced into the germline of the animal, or an ancestor of the animal, at an early developmental stage. The genetic alteration in transgenic animals is stably incorporated into the genome as a result of intentional experimental intervention. Typically, this results from the addition of exogenous foreign DNA or novel constructs (Palmiter et al. 1986. Ann. Rev. Genet. 20:465). With the advent of embryonic stem (ES) cells and specific gene targeting, the definition of transgenesis now includes specific modification of endogenous gene sequences by direct experimental manipulation and by stable incorporation of DNA that codes for effector molecules that modulate the expression of endogenous genes (Gossler et al. 1986. Proc. Natl. Acad. Sci. USA. 83:9065; Schwarzberg et al. 1989. Science 246:799; Joyner et al. 1989. Nature 338:153).

One preferred approach for generating a transgenic animal involves micro-injection of naked DNA into a cell, preferentially into a pronucleus of an animal at an early embryonic stage (usually the zygote/one-cell stage). DNA injected as described integrates into the native genetic material of the embryo, and will faithfully be replicated together with the chromosomal DNA of the host organism. This allows the transgene to be passed to all cells of the developing organism including the germ line. Transgene DNA that is transmitted to the germ line gives rise to transgenic offspring. If transmitted in a Mendelian fashion, half of the offspring will be transgenic. All transgenic animals derived from one founder animal are referred to as a transgenic line. If the injected transgene DNA integrates into chromosomal DNA at a stage later than the one cell embryo not all cells of the organism will be transgenic, and the animal is referred to as being genetically mosaic. Genetically mosaic animals can be either germ line transmitters or non-transmitters. The general approach of microinjection of heterologous DNA constructs into early embryonic cells is usually restricted to the generation of dominant effects, i.e., one allele of the transgene (hemizygous) causes expression of a phenotype (Palmiter et al. 1986. Ann. Rev. Genetics 20:465.)

In another preferred approach, animals are genetically altered by embryonic stem (ES) cell-mediated transgenesis (Gossler et al. 1986, Proc. Natl. Acad. Sci. USA. 83:9065). ES cell lines are derived from early embryos, either from the inner cell mass (ICM) of a blastocyst (an embryo at a relatively early stage of development) or migrating primordial germ cells (PGC) in the embryonic gonads. They have the potential to be cultured in vitro over many passages (i.e. are conditionally immortalized), and they are pluripotent, or totipotent (i.e. are capable of differentiating and giving rise to all cell types. ES cells can be introduced into a recipient blastocyst which is transferred to the uterus of a foster mother for development to term. A recipient blastocyst injected with ES cells can develop into a chimeric animal, due to the contributions from the host embryo and the embryonic stem cells. ES cells can be transfected with heterologous gene constructions that may cause either dominant effects, inactivate whole genes or introduce subtle changes including point mutations. Subsequent to clonal selection for defined genetic changes, a small number of ES cells can be reintroduced into recipient embryos (blastocysts or morulae) where they potentially differentiate into all tissues of the animal including the germ line and thus, give rise to stable lines of animals with designed genetic modifications. Totipotent porcine embryonic stem cells can be genetically altered to have a heterozygous (+/−) mutant, preferably null mutant allele, particularly one produced by homologous recombination in such embryonic stem cells. Alternatively, gene targeting events by homologous recombination can be carried out at the same locus in two consecutive rounds yielding clones of cells that result in a homozygous (−/−) mutant, preferably a null mutant (Ramirez-Solis et al. 1993. Methods in Enzymol. 225:855).

In one preferred embodiment of this invention a DNA sequence is integrated into the native genetic material of the swine and produces antisense RNA that binds to and prevents the translation of the native mRNA encoding α(1,3) galactosyltransferase in the transgenic swine.

In a particularly preferred embodiment the genome of the transgenic swine is modified to include a construct comprising a DNA complementary to that portion of the α(1,3) galactosyltransferase coding region that will prevent expression of all or part of the biologically active enzyme. As the term is used "integrated antisense sequence" means a non-native nucleic acid sequence integrated into the genetic material of a cell that is transcribed (constitutively or inducibly) to produce an mRNA that is complementary to and capable of binding with an mRNA produced by the genetic material of the cell so as to regulate or inhibit the expression thereof.

In another embodiment of the invention, cells or cell lines from non-mutant swine are made with the α(1,3) galactosyltransferase inactivated on one or both alleles through the use of an integrated antisense sequence which binds to and prevents the translation of the native mRNA encoding the α(1,3) galactosyltransferase in said cells or cell lines. The integrated antisense sequence, such as the RNA sequence transcribed in Example 3 is delivered to the cells by various means such as electroporation, retroviral transduction or lipofection.

In another preferred embodiment, the transgenic swine is made to produce a ribozyme (catalytic RNA) that cleaves the α(1,3) galactosyltransferase mRNA with specificity. Ribozymes are specific domains of RNA which have enzymatic activity, either acting as an enzyme on other RNA molecules or acting intramolecularly in reactions such as self-splicing or self-cleaving (Long, D. M. and Uhlenbeck, O. C. 1993. FASEB Journal. 7:25–30). Certain ribozymes contain a small structural domain generally of only about 30 nucleotides called a "hammerhead". The hammerhead is a loop of RNA that is flanked by two linear domains that are specific complements to domains on the substrate to be cleaved. The site on the hammerhead ribozyme that effects the cleavage of substrate is the base of the stem loop or hammerhead. As shown in FIG. 3, the ribozymes of the present invention have flanking sequences complementary to domains near the 5' end of the α(1,3) galactosyltransferase cDNA gene.

The DNA for the ribozymes is integrated into the genetic material of an animal, tissue or cell and is transcribed (constitutively or inducibly) to produce a ribozyme which is capable of selectively binding with and cleaving the α(1,3) galactosyltransferase mRNA. As it is a catalytic molecule, each such ribozyme is capable of cleaving multiple substrate molecules.

The catalytic "stem loop" of the ribozyme is flanked by sequences complementary to regions of the α(1,3) galactosyltransferase mRNA. In a particularly preferred embodiment the transgenic swine is modified to integrate a construct comprising the DNA coding for that portion of catalytic RNA necessary to inactivate the mRNA of the α(1,3) galactosyltransferase operably linked to a promoter therefor.

In another preferred embodiment, using cultured porcine embryonic stem cells, a mutation, preferably a null mutation is introduced by gene targeting at the native genomic locus encoding α(1,3) galactosyltransferase. Gene targeting by homologous recombination in ES cells is performed using constructs containing extensive sequence homology to the native gene, but specific mutations at positions in the gene which are critical for generating a biologically active protein. Therefore, mutations can be located in regions important for either translation, transcription or those coding for functional domains of the protein. Selection for ES clones that have homologously recombined a gene targeting construct, also termed gene "knock out" construct, can be achieved using specific marker genes. The standard procedure is to use a combination of two drug selectable markers including one for positive selection (survival in the presence of drug, if marker is expressed) and one for negative selection (killing in the presence of the drug, if marker is expressed) (Mansour et al., 1988. Nature 336:348) One preferred type of targeting vector includes the neomycin phosphotransferase (neo) gene for positive selection in the drug G418, as well as the Herpes Simplex Virus-thymidine kinase (HSV-tk) gene for selective killing in gancyclovir. Drug selection in G418 and gancyclovir, also termed positive negative selection (PNS) (Mansour et al. 1988. Nature 336:348; Tubulewicz et al. 1991. Cell 65:1153) allows for enrichment of ES cell clones that have undergone gene targeting, rather than random integration events. Confirmation of homologous recombination events is performed using Southern analysis.

The design of the α(1,3) galactosyltransferase targeting construct is described in Example 4. The procedure as applied here uses a positive selection (survival) based on integration of the neo (neomycin resistance), preferably in inverse orientation to the endogenous α(1,3) galactosyltransferase gene locus in a cassette with the phosphoglycerate kinase (PGK-1) promoter and with flanking oligonucleotides complementary to two separate regions of the α(1,3) galactosyltransferase gene sequence. It is understood that other positive selectable markers may be used instead of neo. The neo gene is linked with its promoter to be under control thereof. Downstream from the second flanking sequence is the HSV-tk gene which, if integrated into the genome encodes for production of thymidine kinase making the cell susceptible to killing by gancyclovir (negative selection). The integration of the neo gene but not the HSV-tk gene occurs only where integration into the α(1,3) galactosyltransferase gene has occurred and provides for both positive and negative selection of the cells so transformed.

In another embodiment of the invention, cells or cell lines from non-mutant swine are made with the α(1,3) galactosyltransferase inactivated on one or both alleles through the use of an integrated ribozyme sequence which binds to and cleaves the native mRNA encoding the α(1,3) galactosyltransferase in said cells or cell lines. The integrated ribozyme sequence, such as the RNA sequence transcribed in Example 4 is delivered to the cells by various means such as electroporation, retroviral transduction or lipofection.

The swine is preferably an α(1,3) galactosyltransferase negative swine grown from a porcine oocyte whose pronuclear material has been removed and into which has been introduced a totipotent porcine embryonic stem cell using protocols for nuclear transfer (Prather et al. 1989, Biol. Reprod. 41:414) ES cells used for nuclear transfer are negative for the expression of α(1,3) galactosyl transferase, or alternatively, totipotent ES cells used for nuclear transfer are mutated in a targeted fashion in at least one allele of the α(1,3) galactosyltransferase gene.

The swine is preferably lacking expression of the α(1,3) galactosyltransferase gene and bred from chimeric animals which were generated from ES cells by blastocyst injection or morula aggregation. ES cells used to generate the preferably null-mutated chimeric animal were mutated at least in one allele of the α(1,3) galactosyltransferase gene locus, using gene targeting by homologous recombination.

A chimeric swine is preferably constituted by ES cells mutated in one allele of the α(1,3) galactosyltransferase gene. Derived from mutated ES cells are also germ cells, male or female gametes that allow the mutation to be passed to offspring, and allow for breeding of heterozygous mutant sibling pigs to yield animals homozygous mutant at the α(1,3) galactosyltransferase locus. Also described is a swine, deficient for an α(1,3) galactosyltransferase protein (i.e., characterized by lack of expression of α(1,3) galactosyltransferase protein) and have little, if any, functional Galα1-3Galβ1-4GlcNAc epitope-containing carbohydrate antigen on the cell surface are produced. Further described are methods of producing transgenic swine and methods of producing tissue from heterozygous swine or homozygous swine of the present invention. The present invention also relates to cell lines, such as swine cell lines, in which the α(1,3) galactosyltransferase gene is inactivated on one or both alleles and use of such cell lines as a source of tissue and cells for transplantation.

Tissues, organs and purified or substantially pure cells obtained-from transgenic swine, more specifically from hemizygous, heterozygous or homozygous mutant animals of the present invention can be used for xenogeneic transplantation into other mammals including humans in which tissues, organs or cells are needed. The α(1,3) galactosyltransferase inactive cells can themselves be the treatment or therapeutic/clinical product. For example, keratinocytes rendered α(1,3) galactosyltransferase inactive can be used for macular degeneration and pancreatic cells rendered α(1,3) galactosyltransferase deficient can be used to replace or restore pancreatic products and functions to a recipient. In another embodiment, α(1,3) galactosyltransferase inactive cells produced by the present method are further manipulated, using known methods, to introduce a gene or genes of interest, which encode(s) a product(s), such as a therapeutic product, to be provided to a recipient. In this embodiment, the α(1,3) galactosyltransferase deficient tissue, organ or cells serve as a delivery vehicle for the encoded product(s). For example, α(1,3) galactosyltransferase deficient cells, such as fibroblasts or endothelial cells, can be transfected with a gene encoding a therapeutic product, such as cytokines that augment donor tissue engraftment, Factor VIII, Factor IX, erythropoietin, insulin, human major histocompatibility (MHC) molecules or growth hormone, and introduced into an individual in need of the encoded product.

Alternatively, recipient blastocysts are injected or morulae are aggregated with totipotent embryonic stem cells yielding chimeric swine containing at least one allele of a mutated, preferably null-mutated α(1,3) galactosyltransferase gene produced by homologous recombination. A chimeric swine is preferably constituted by ES cells mutated in one allele of the α(1,3) galactosyltransferase gene. Derived from mutated ES cells are also germ cells that allow the mutation to be passed to offspring, and breeding of heterozygous mutant sibling pigs to yield animals homozygous mutant at the α(1,3) galactosyltransferase locus. Also described is a swine, deficient for an α(1,3) galactosyltransferase protein (i.e., characterized by essentially no expression of α(1,3) galactosyltransferase protein) and with little, if any, functional Galα1-3Galβ1-4GlcNAc epitope-containing carbohydrate antigen on the cell surface are produced. Further described are methods of producing transgenic swine and methods of producing tissue from heterozygous swine or homozygous swine of the present invention. The present invention also related to cell lines, such as swine cell lines, in which the α(1,3) galactosyltransferase gene is inactivated on one or both alleles and use of such cell lines as a source of tissue, organs and cells for transplantation.

FIG. 1 illustrates the complete cDNA sequence of the α(1,3) galactosyltransferase gene (SEQ. ID. No. 1), having an open reading frame of 1113 base pairs, encoding a 371 amino acid protein.

FIG. 2 compares the protein sequences encoded by the porcine, bovine and murine α(1,3) galactosyltransferase cDNA genes.

FIG. 3 illustrates the secondary structure of a trans-acting hammerhead ribozyme targeted to α(1,3) galactosyltransferase mRNA.

A method of producing a chimeric swine and porcine organs and tissue cultures, homozygous for an α(1,3) galactosyltransferase gene inactivation, in which α(1,3) galactosyltransferase protein synthesis and cell surface Galα1-3Galβ1-4GlcNAc epitope-containing carbohydrate cell surface markers expression are deficient is disclosed. Of particular interest are purified cell types which have been rendered deficient in α(1,3) galactosyltransferase expression. Such cell types include fibroblasts, keratinocytes, myoblasts and endothelial cells.

In one embodiment of the present invention, swine cells altered as described herein are used to provide cells needed by a recipient or to provide gene therapy. The cells, which are deficient in Galα(1-3)Galβ1-4GlcNAc epitope-containing carbohydrates cell surface antigen, are cultured and transplanted to an oocyte.

The embryonic stem cells with the null mutant α(1,3) galactosyltransferase locus are introduced into swine blastocysts, which are then introduced into a pseudopregnant swine. The embryo develops into a chimeric swine offspring. When bred with wild-type females, chimeric males transmit the α(1,3) galactosyltransferase inactivation in the embryonic stem cell to their offspring, which are heterozygous for the inactivation. Swine heterozygous for the α(1,3) galactosyltransferase gene inactivation can be intercrossed to produce swine homozygous (−/−) for the mutation.

Purified or substantially pure α(1,3) galactosyltransferase deficient cells can be obtained from tissues or transgenic or chimeric swine produced as described herein. Alternatively, they can be obtained from a normal (non-altered) donor swine and altered using a method described herein. These cells can be then cultured by known methods to produce a quantity of cells useful for transplantation. In addition, cell lines, such as swine cell lines, in which the α(1,3) galactosyltransferase gene is disrupted, preferably on both alleles, are useful as a source of tissue and cells for transplantation.

EXAMPLE 1

ISOLATION AND CHARACTERIZATION OF PORCINE α(1,3) GALACTOSYLTRANSFERASE cDNA

A previously described λZAP II porcine spleen cDNA library (Gustafsson et al. 1990. Proc. Natl. Acad. Sci. USA. 87:9798–9802) was screened by hybridization with a cloned α(1,3) galactosyltransferase cDNA probe (Joziasse et al. 1989. J. Biol. Chem. 264:14290–14297) The Genbank Accession number for the bovine α(1,3) galactosyltransferase cDNA sequence is J04989. The bovine α(1,3) galactosyltransferase cDNA probe was kindly provided by Dr. David Joziasse, University of Leiden, The Netherlands. The probe was radioactively labeled with a $^{32}$P-dATP using the Megaprime DNA labeling system (Amersham International, UK). Positive clones were confirmed by the polymerase chain reaction (PCR), using primers (SEQ. ID. NO: 2 and SEQ. ID. NO: 3) derived from the bovine α(1,3) galactosyltransferase cDNA sequence. SEQ. ID. NO: 2 corresponds to bovine α(1,3) galactosyltransferase nucleotides 712–729 and SEQ. ID. NO: 3 corresponds to the reverse complement of bovine α(1,3) galactosyltransferase nucleotides 1501–1508. Recombinant pBluescript plasmids from positive clones were automatically excised with the helper phage R408 (Stratagene Ltd., Cambridge, UK) and amplified in *E. coli* strain TG1 (ATCC 39078). Plasmid DNA was prepared using the Magic Miniprep kit (Promega Ltd., Southampton, UK) following the manufacturer's instructions and the DNA was characterized by cleavage with EcoRI. DNA sequencing was performed by the dideoxy chain termination method, using a T7 DNA polymerase sequencing kit (Pharmacia Biosystems Ltd., Milton Keynes, UK) according to the manufacturer's instructions. The synthetic oligonucleotide primers SEQ. ID. NOs. 4–12 were used. SEQ. ID. NO. 4 is Stratagene SK, catalog number 300305, (Stratagene Inc., La Jolla, Calif.). SEQ. ID. NO: 5 corresponds to the reverse complement of porcine α(1,3) galactosyltransferase nucleotides 94–111. SEQ. ID. NO: 6 corresponds to the porcine α(1,3) galactosyltransferase nucleotides 163–180. SEQ. ID. NO: 7 corresponds to the reverse complement of porcine α(1,3) galactosyltransferase nucleotides 442–459. SEQ. ID. NO: 8 corresponds to the complement of porcine and bovine α(1,3) galactosyltransferase nucleotides 538–555 and 982–999, respectively. SEQ. ID. NO: 9 corresponds to the reverse complement of porcine α(1,3) galactosyltransferase nucleotides 596–615. SEQ. ID. NO: 10 corresponds to the porcine α(1,3) galactosyltransferase nucleotides 682–699. SEQ. ID. NO: 11 corresponds to the porcine α(1,3) galactosyltransferase nucleotides 847–864. SEQ. ID. NO: 12 corresponds to the reverse complement of porcine α(1,3) galactosyltransferase nucleotides 970–987.

Four positive clones were obtained from approximately $2 \times 10^4$ plaques screened by hybridization with the bovine α(1,3) galactosyltransferase cDNA probe (Joziasse et al. 1989. J. Biol. Chem. 264:14290–14297). Three of these clones were confirmed to be positive by PCR. Each of the three recombinant pBluescript plasmids, generated by automatic excision from λZapII with helper phage, contained inserts of approximately 2.5 kb as determined by EcoRI cleavage. One clone, designated pSα13GT1, was selected for further study.

DNA sequence analysis of pSα13GT1 revealed an open reading frame of 1113 bases (See SEQ. ID. NO: 1 and FIG. 1) showing 86% identity with the published bovine cDNA sequence (Joziasse et al. 1989. J. Biol. Chem. 264:14290–14297) and encoding a 371 amino acid protein with 85% and 76% identity with the bovine and murine α(1,3) galactosyltransferase amino acid sequences, respectively (FIG. 2).

EXAMPLE 2

ANTISENSE OLIGONUCLEOTIDE INHIBITION OF α(1,3) GALACTOSYLTRANSFERASE EXPRESSION

Three antisense 5' and 3' phosphothioate-protected oligonucleotides (S-oligonucleotides, SEQ. ID. NOs 13–15) are tested in an in vitro system employing porcine primary endothelial cell cultures (from porcine aorta) and a porcine B-cell line (L231, European Collection of Animal Cell Cultures, PHLS, Center for Applied Microbiology and Research, Porton Down, Salisbury, UK). SEQ. ID. NO: 13 corresponds to the reverse complement of porcine α(1,3) galactosyltransferase cDNA nucleotides 16–35. SEQ. ID. NO: 14 corresponds to the reverse complement of porcine α(1,3) galactosyltransferase cDNA nucleotides 31–53. SEQ. ID. NO: 15 corresponds to the reverse complement of porcine α(1,3) galactosyltransferase cDNA nucleotides 6–23. All three antisense oligonucleotides are directed at the 5' region of the mRNA surrounding the initiation of translation. Nonsense S-oligonucleotides randomized from the antisense sequence are used as controls at similar molar concentrations.

Porcine endothelial cells are derived from miniature swine aorta by scraping the luminal surface of the blood vessel as described (Ryan et al. Tissue and Cell 12:619–635). The cells are suspended in M199 medium supplemented with 20% fetal bovine serum (GIBCO BRL, Gaithersburg, Md.) and gentamycin and plated in 25 cm² tissue culture flasks, pre-coated with fibronectin (5 µg/cm²) and laminin (1 µg/cm²). Endothelial cell growth supplement (Collaborative Research, Bedford, Mass.) at 150 µg/ml is added at the beginning of the culture. The cultures are maintained by changing one half of the medium every 2–3 days. The porcine lymphoblastoid cell line L231 is maintained in DMEM, 10% fetal bovine serum, 10% NCTC-109, 1% glutamine, 1% pen-strep (all from GIBCO BRL, Gaithersburg, Md.) and $5 \times 10^{-2}$ M 2-mercaptoethanol (Sigma, St. Louis, Mo.). The L231 cells are subcultured by splitting the cells 1:3 every three days.

For cell treatment, S-oligonucleotides are added, to a final concentration of 5–10 µM, to growing cells at 24 hr intervals, typically for 48 hr, and then the treated cells are examined for the levels of α(1,3) galactosyltransferase mRNA (by Northern blot analysis) and expression of the epitope on the cell surface by human AB serum and FITC-labeled mouse anti-human secondary reagents (anti-human IgM and IgG).

EXAMPLE 3

PREPARATION AND USE OF INTEGRATED ANTISENSE CONSTRUCTS

We are studying the ability of integrated antisense constructs to inhibit specifically the production of the porcine α(1,3) galactosyltransferase. Specific inhibition of the α(1,3) galactosyltransferase in transfected cells allows assessment of the contribution of the enzyme in the hyperacute phenomenon. Vectors are constructed to express the α(1,3) galactosyltransferase antisense mRNA, under the control of the cytomegalovirus (CMV) promoter. Specifically, pSα13GT1 is cleaved with NotI and EcoRV which generates a restriction fragment of length 537 bp, containing part of the pBluescript polylinker sequence through to nucleotide 531 of the α(1,3) galactosyltransferase cDNA sequence. This DNA fragment is cloned into the expression vector pcDNA3 (Invitrogen, San Diego, Calif.), cleaved with the same enzymes. The resulting vector therefore contains the porcine α(1,3) galactosyltransferase sequence in the anti-sense direction, relative to the CMV promoter located in pcDNA3. The construct is transfected, using electroporation or other high efficiency methods for introducing DNA into mammalian cells, into both porcine endothelial cells and the L231 porcine lymphoblastoid cell lines (grown as described in Example 2). The effect of the antisense RNA is monitored by both Northern blot analysis of mRNA of the α(1,3) galactosyltransferase gene and the degree of binding of human serum components (i.e., natural antibodies).

EXAMPLE 4

RIBOZYME SEQUENCES THAT INACTIVATE PORCINE α(1,3) GALACTOSYLTRANSFERASE mRNA

This example describes a method for construction of the vectors which encode ribozyme sequences which are specifically designed to cleave the porcine α(1,3) galactosyltransferase mRNA sequence.

The design of the ribozyme sequences is based upon the consensus cis-acting hammerhead ribozyme sequence (Ruffner et al. 1990. Biochemistry 29:10695–10702). We used the Zuker algorithm in the suite of programs available from the Genetics Computer Group (Madison, Wis.) to model the cis-acting hammerhead ribozyme sequences (Denman, R. B. 1993. BioTechniques 15:1090–1095). Ribozyme target sequences are identified within the α(1,3) galactosyltransferase mRNA sequence. A ribozyme sequence file for each potential ribozyme sequence is generated based on the target sequence and using five nucleotides to connect the mRNA target sequence with the catalytic strand of the ribozyme. The sequence file is then folded into the lowest energy structure using RNAFOLD. Sequences which have non-ribozyme structures are discarded. FIG. 3 illustrates one of the ribozyme-target RNA secondary structures, using the ribozyme corresponding to SEQ. ID. NO. 16. The small arrow indicates the cleavage site on the mRNA, between stem I and stem III.

Synthetic oligonucleotides to encode the ribozymes (SEQ. ID. NOs. 16–21) are made on an Applied BioSystems Oligonucleotide synthesizer (Foster City, Calif.) with termini corresponding to the overhangs of the restriction endonucleases NotI and XbaI. The duplex DNA is cloned into the mammalian expression cloning vector pcDNA3 (Invitrogen, Calif.). Expression of the ribozyme is under the control of the CMV promoter present in pcDNA3. The transcripts consist of approximately 140 nucleotides both 5' and 3' to the ribozyme sequence. The expression level of the transcribed sequence is ascertained by Northern blot analysis. If the RNA level is low additional sequences will be included in the construct in order to generate a longer and more stable transcript.

The construct is transfected using the electroporation technique into porcine primary endothelial cells, porcine B cells (L231). Also, the vector is co-transfected with plasmid expressing the porcine α(1,3) galactosyltransferase into COS7 cells. Since COS7 cells do not express an endogenous α(1,3) galactosyltransferase, the effect of the presence of the ribozyme on the expression of the introduced porcine α(1,3) galactosyltransferase gene is easily ascertained.

EXAMPLE 5

TRANSGENIC SWINE PRODUCING ANTISENSE OR RIBOZYME RNA THAT INHIBIT α(1,3) GALACTOSYLTRANSFERASE SYNTHESIS

This approach requires direct microinjection of transgene DNA into one of the pronuclei of a porcine embryo at the zygote stage(one-cell embryo). Injected one-cell embryos are transferred to recipient foster gilts for development to term (Hammer et al. 1985, Nature 315:680; Pursel et al. 1989, Science 244:1281)

Critical to successfully accomplishing this approach is the age and weight of the donor pigs, preferentially the haplotype specific mini-swine. Optimally, the animals are of age 8 to 10 months and weigh 70 to 85 lbs. This increases the probability of obtaining adequate supply of one-cell embryos for microinjection of the transgenes. In order to allow for accurate timing of the embryo collections at that stage from a number of embryo donors, the gilts are synchronized using a preparation of synthetic progesterone (Regumate). Hormone implants are applied to designated gilts 30 days prior to the date of embryo collection. Twenty days later, ten days prior to the date of collection, the implants are removed and the animals are treated with additional hormones to induce superovulation i.e. to increase the number of embryos for microinjection. Three days following implant removal, the animals are treated with 400 to 1000 IU of pregnant mare serum gonadotropin (PMSG) and with 750 IU of human chorionic gonadotropin (hCG) three to four days later. These animals are bred by artificial insemination (AI) on two consecutive days following injection of hCG.

Embryo collections are performed as follows: three days following the initial injection of hCG, the animals are anesthetized with an intramuscular injection of Telazol (3 mg/lb.), Rompum (2 mg/lb.) and Atropine (1 mg/lb.). A midline laparotomy is performed and the reproductive tract exteriorized. Collection of the zygotes is performed by cannulating the ampulla of the oviduct and flushing the oviduct with 10 to 15 ml phosphate buffered saline, prewarmed to 39° C. Following the collection, the donor animals are prepared for recovery from surgery according to USDA guidelines. Animals used twice for embryo collections are euthanized according to USDA guidelines.

Injection of the transgene DNA into the pronuclei of the zygotes is carried out as follows. Zygotes are maintained in HAM's F-12 medium supplemented with 10% fetal calf serum at 38° C. in 5% $CO_2$ atmosphere. For injection the zygotes are placed into modified BMOC-2 medium containing HEPES salts (Ebert et al. 1984. J. Embryol. Exp. Morph. 84:91–103), centrifuged at 13,000×g to partition the embryonic lipids and visualize the pronuclei. The embryos are placed in an injection chamber (depression slide) containing the same medium overlaid with light paraffin oil. Microinjection is performed on a Nikon Diaphot invertedmicroscope equipped with Nomarski optics and Narishige micro-manipulators. Using 40x lens power the embryos are held in place with a holding pipette and injected with a glass needle which is back-filled with the solution of DNA containing the transgene (2 µg/ml). Injection of approximately 2 picoliters of the solution (4 femptograms of DNA) which is equivalent to around 500 copies of the transgene is monitored by the swelling of the pronucleus by about 50%. Embryos that are injected are placed into the incubator prior to transfer to recipient animals.

Recipient animals are prepared similar to the donor animals, but not superovulated. Prior to the transfer of the injected embryos, recipient gilts are anesthetized, the abdomen opened surgically by applying a longitudinal incision and the ovaries exteriorized. The oviduct ipsilateral to the ovary with the larger number of corpus lutei is flushed, the embryos checked to evaluate if the animals is reproductively sound. Approximately 4 to 6 zygotes injected with the transgene are transferred to the flushed oviduct, the abdominal incision sutured and the animals placed in a warm area for recovery. The status of the pregnancy is monitored by ultrasound starting at day 25, or approximately one week following the expected date of implantation. Pregnant recipients are housed separately until they are due to farrow.

Newborn piglets are analyzed for integration of the transgene into chromosomal DNA. Genomic DNA is extracted from an ear punch or a blood sample and initial screening is performed using PCR. Animals that are potentially transgene-positive are confirmed by Southern analysis. Transgenic founder animals are subjected to further analysis including the levels of expression, phenotype and germ line transmission. Northern analysis from RNA of selective tissues including endothelial cells is performed to determine the level of transgene expression. Also, immunological assays including flow cytometric analysis for binding of antibody from human serum and complement mediated lysis of pig cells recognized by human natural antibodies are carried out to evaluate the transgene effect. Animals that satisfy the above criteria are used as founders for breeding of a transgenic line. If the founder transgenic animals only satisfy part of the requirements, breeding and specific intercrossing of transgenic offspring is performed to assay the transgene effect in homozygous animals.

EXAMPLE 6

A SWINE MADE NULL-MUTANT FOR α(1,3) GALACTOSYLTRANSFERASE BY HOMOLOGOUS RECOMBINATION

Gene targeting by homologous recombination in swine requires several components, including the following: (A) a mutant gene targeting construct including the positive/ negative drug-selectable marker genes (Tubulewicz et al. 1991. Cell 65:1153); (B) embryonic stem cell cultures; and (C) the experimental embryology to reconstitute an animal from the cultured cells.

The targeting construct is provided from a genomic clone that spans most of the α(1,3) galactosyltransferase gene and is isolated from a library made of isogenic DNA from a major histocompatibility complex (MHC) haplotype d/d of the miniature swine. Fragments of that genomic clone are introduced into a positive/negative selectable marker cassette specifically developed for gene targeting in embryonic stem (ES) cells and termed pPNT (Tubulewicz et al. 1991. Cell 65:1153). This gene targeting cassette includes as positive selectable marker the bacterial neomycin phosphotransferase gene (neo) which allows for selection of cells in G418. The neo gene is regulated by a promoter that guarantees high level expression in ES cells such as the phosphoglycerate kinase promoter-1 (PGK-1). Negative selection is accomplished by expressing the Herpes Simplex Virus—thymidine kinase (HSV-tk) gene which allows for selective killing of cells in Gancyclovir. Similar to the neo gene, the HSV-tk gene is regulated by the PGK-1 promoter, as well. In the targeting cassette PPNT there are unique and convenient cloning sites between the neo and the HSV-tk gene which are suitable sites to introduce the genomic fragment of the α(1,3) galactosyltransferase gene upstream of the translation initiation signal AUG (e.g. SalI sites in introns 2 and 4) This fragment of approximately 2 kb of DNA is cloned in reverse orientation to the direction of transcription of the PGK-neo cassette to assure that no truncated or residual peptide is generated at the α(1,3) galactosyltransferase-locus. Genomic sequences of the α(1, 3) galactosyltransferase locus downstream of exon 4, approximately 5 kb are introduced into PPNT at the 5'-end of the neo gene. This targeting construction termed pPNT-alpha GT1 is linearized and transfected by electroporation into porcine ES cells. Double selection in G418 (150 to 300 µg/ml) and Gancyclovir is performed to initially isolate clones of ES cells with targeted mutations in the α(1,3) galactosyltransferase locus. Confirmation of homologous recombinant clones is achieved using Southern analysis.

ES cell clones that have undergone targeted mutagenesis of one allele of the α(1,3) galactosyltransferase locus are subjected to a second round of in vitro mutagenesis or used for reconstituting an animal that contains the mutation. A second round of in vitro mutagenesis can be carried out using an analogous targeting construction with hygromycin phosphotransferase hyg as positive selectable marker gene.

As far as the reconstitution of animals is concerned, the methods include nuclear transfer, blastocyst injection or morula aggregation. The preferred routes include either blastocyst injection or morula aggregation which yield chimeras between the donor cells and the recipient embryos. For both these methods recipient embryos are prepared as follows: embryo donor/recipient gilts are synchronized and mated as described in Example 5. On day 6 following artificial insemination or natural mating, the gilts are prepared for surgery as described earlier, anesthetized and the uteri retrogradely flushed using a prewarmed (38° C.) solution of phosphate buffered saline (PBS). Intact blastocysts that are encapsulated by the zona pellucida are placed in a depression slide containing HEPES-buffered medium (Whitten's or TL-HEPES) and approximately 15 to 20 ES cells are injected into the blastocoel using a glass injection needle with an opening of 20 μm and Narishige micromanipulators. Injected embryos are then reimplanted into recipient foster gilts for development to term and pregnancies are monitored using ultrasound. Offspring is analyzed for chimerism using the polymerase chain reaction (PCR) of DNA samples extracted from blood, skin and tissue biopsies and primers complementary to the neo or hyg gene. Germ line transmission of the chimeras is assayed using PCR and in situ hybridization of tissue samples obtain from male and female gonads. Male and female chimeras which transmit the ES cell genotype to the germ line are crossed to yield homozygously mutant animals. Analysis of mutant animals for expression of α(1,3) galactosyltransferase and binding of human natural antibodies to endothelial cells of those animals is used as final test to assess the validity of gene knock out approach in swine.

What is claimed is:

1. Porcine cells, in vitro, said cells comprising a disrupted α(1,3)-galactosyltransferase gene encoding the polypeptide of SEQ.ID.NO:1, whereby expression of functional α(1,3)-galactosyltransferase is inhibited.

2. The cells of claim 1 wherein said gene is disrupted by homologous recombination.

3. The cells of claim 1 wherein the Galα1-3 Galα1-4 GlcNAc epitope is not presented on the cell surface.

4. A process for producing a modified porcine cell, comprising:
    treating a porcine cell, in vitro, said treating introducing a disruption into the α(1,3)-galactosyltransferase gene encoding the polypeptide of SEQ.ID.NO:1, whereby expression of functional α(1,3)-galactosyltransferase is inhibited.

5. The process of claim 4 wherein said gene is disrupted by homologous recombination.

* * * * *

UNITED STATES PATENT AND TRADEMARK OFFICE
CERTIFICATE OF CORRECTION

PATENT NO. : 6,153,428  
DATED : March 26, 1996  
INVENTOR(S) : Gustaffsson et al.

It is certified that error appears in the above-identified patent and that said Letters Patent is hereby corrected as shown below:

<u>Title page,</u>
Assignee, change from "BioTransplant Inc., Charlestown, Mass." to
-- University of London, London England; The General Hospital Corporation, Boston, Mass. --

Signed and Sealed this

Twelfth Day of March, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 1269 bases
      (B) TYPE: nucleic acid
      (C) STRANDEDNESS: single
      (D) TOPOLOGY: linear (iii) HYPOTHETICAL: NO (iv) ANTI-SENSE: NO (xi) SEQUENCE DESCRIPTION: SEQ ID NO: 1:

```
CATGAGGAGA AAATA ATG AAT GTC AAA GGA AGA GTG GTT CTG TCA ATG          48
              Met Asn Val Lys Gly Arg Val Val Leu Ser Met
                1               5                  10

CTG CTT GTC TCA ACT GTA ATG GTT GTG TTT TGG GAA TAC ATC AAC AGC       96
Leu Leu Val Ser Thr Val Met Val Val Phe Trp Glu Tyr Ile Asn Ser
            15                  20                  25

CCA GAA GGT TCT TTG TTC TGG ATA TAC CAG TCA AAA AAC CCA GAA GTT      144
Pro Glu Gly Ser Leu Phe Trp Ile Tyr Gln Ser Lys Asn Pro Glu Val
        30                  35                  40

GGC AGC AGT GCT CAG AGG GGC TGG TGG TTT CCG AGC TGG TTT AAC AAT      192
Gly Ser Ser Ala Gln Arg Gly Trp Trp Phe Pro Ser Trp Phe Asn Asn
    45                  50                  55

GGG ACT CAC AGT TAC CAC GAA GAA GAA GAC GCT ATA GGC AAC GAA AAG      240
Gly Thr His Ser Tyr His Glu Glu Glu Asp Ala Ile Gly Asn Glu Lys
60                  65                  70                  75

GAA CAA AGA AAA GAA GAC AAC AGA GGA GAG CTT CCG CTA GTG GAC TGG      288
Glu Gln Arg Lys Glu Asp Asn Arg Gly Glu Leu Pro Leu Val Asp Trp
                80                  85                  90

TTT AAT CCT GAG AAA CGC CCA GAG GTC GTG ACC ATA ACC AGA TGG AAG      336
Phe Asn Pro Glu Lys Arg Pro Glu Val Val Thr Ile Thr Arg Trp Lys
            95                 100                 105

GCT CCA GTG GTA TGG GAA GGC ACT TAC AAC AGA GCC GTC TTA GAT AAT      384
Ala Pro Val Val Trp Glu Gly Thr Tyr Asn Arg Ala Val Leu Asp Asn
        110                 115                 120

TAT TAT GCC AAA CAG AAA ATT ACC GTG GGC TTG ACG GTT TTT GCT GTC      432
Tyr Tyr Ala Lys Gln Lys Ile Thr Val Gly Leu Thr Val Phe Ala Val
    125                 130                 135

GGA AGA TAC ATT GAG CAT TAC TTG GAG GAG TTC TTA ATA TCT GCA AAT      480
Gly Arg Tyr Ile Glu His Tyr Leu Glu Glu Phe Leu Ile Ser Ala Asn
```

```
140              145              150              155
ACA TAC TTC ATG GTT GGC CAC AAA GTC ATC TTT TAC ATC ATG GTG GAT      528
Thr Tyr Phe Met Val Gly His Lys Val Ile Phe Tyr Ile Met Val Asp
                    160              165              170

GAT ATC TCC AGG ATG CCT TTG ATA GAG CTG GGT CCT CTG CGT TCC TTT      576
Asp Ile Ser Arg Met Pro Leu Ile Glu Leu Gly Pro Leu Arg Ser Phe
            175              180              185

AAA GTG TTT GAG ATC AAG TCC GAG AAG AGG TGG CAA GAC ATC AGC ATG      624
Lys Val Phe Glu Ile Lys Ser Glu Lys Arg Trp Gln Asp Ile Ser Met
            190              195              200

ATG CGC ATG AAG ACC ATC GGG GAG CAC ATC CTG GCC CAC ATC CAG CAC      672
Met Arg Met Lys Thr Ile Gly Glu His Ile Leu Ala His Ile Gln His
    205              210              215

GAG GTG GAC TTC CTC TTC TGC ATG GAC GTG GAT CAG GTC TTC CAA AAC      720
Glu Val Asp Phe Leu Phe Cys Met Asp Val Asp Gln Val Phe Gln Asn
220              225              230              235

AAC TTT GGG GTG GAG ACC CTG GGC CAG TCG GTG GCT CAG CTA CAG GCC      768
Asn Phe Gly Val Glu Thr Leu Gly Gln Ser Val Ala Gln Leu Gln Ala
                240              245              250

TGG TGG TAC AAG GCA CAT CCT GAC GAG TTC ACC TAC GAG AGG CGG AAG      816
Trp Trp Tyr Lys Ala His Pro Asp Glu Phe Thr Tyr Glu Arg Arg Lys
            255              260              265

GAG TCC GCA GCC TAC ATT CCG TTT GGC CAG GGG GAT TTT TAT TAC CAC      864
Glu Ser Ala Ala Tyr Ile Pro Phe Gly Gln Gly Asp Phe Tyr Tyr His
            270              275              280

GCA GCC ATT TTT GGG GGA ACA CCC ACT CAG GTT CTA AAC ATC ACT CAG      912
Ala Ala Ile Phe Gly Gly Thr Pro Thr Gln Val Leu Asn Ile Thr Gln
    285              290              295

GAG TGC TTC AAG GGA ATC CTC CAG GAC AAG GAA AAT GAC ATA GAA GCC      960
Glu Cys Phe Lys Gly Ile Leu Gln Asp Lys Glu Asn Asp Ile Glu Ala
300              305              310              315

GAG TGG CAT GAT GAA AGC CAT CTA AAC AAG TAT TTC CTT CTC AAC AAA1     008
Glu Trp His Asp Glu Ser His Leu Asn Lys Tyr Phe Leu Leu Asn Lys
                320              325              330

CCC ACT AAA ATC TTA TCC CCA GAA TAC TGC TGG GAT TAT CAT ATA GGC1     056
Pro Thr Lys Ile Leu Ser Pro Glu Tyr Cys Trp Asp Tyr His Ile Gly
            335              340              345

ATG TCT GTG GAT ATT AGG ATT GTC AAG ATA GCT TGG CAG AAA AAA GAG1     104
Met Ser Val Asp Ile Arg Ile Val Lys Ile Ala Trp Gln Lys Lys Glu
            350              355              360

TAT AAT TTG GTT AGA AAT AAC ATC TGA CTTTAAATTG TGCCAGCAGT            1151
Tyr Asn Leu Val Arg Asn Asn Ile
    365              370

TTTCTGAATT TGAAAGAGTA TTACTCTGGC TACTTCTCCA GAGAAGTAGC               1201

ACTTAATTTT AACTTTTAAA AAAATACTAA CAAAATACCA ACACAGTAAG               1251

TACATATTAT TCTTCCTT                                                  1269

(2) INFORMATION FOR SEQ ID NO: 2:

(i) SEQUENCE CHARACTERISTICS:
        (A) LENGTH: 18 bases
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 2:
```

```
AAGCTTAAGC TATCGGAC                                                      18

(2) INFORMATION FOR SEQ ID NO: 3:

(i) SEQUENCE CHARACTERISTICS:
        (A) LENGTH: 18 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 3:

CTTAATATCC GCAGGTAG                                                      18

(2) INFORMATION FOR SEQ ID NO: 4:

(i) SEQUENCE CHARACTERISTICS:
        (A) LENGTH: 20 bases
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 4:

CGCTCTAGAA CTAGTGGATC                                                    20

(2) INFORMATION FOR SEQ ID NO: 5:

(i) SEQUENCE CHARACTERISTICS:
        (A) LENGTH: 18 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 5:

CAAAGAACCT TCTGGGCT                                                      18

(2) INFORMATION FOR SEQ ID NO: 6:

(i) SEQUENCE CHARACTERISTICS:
        (A) LENGTH: 18 bases
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 6:

GGCTGGTGGT TTCCGAGC                                                      18

(2) INFORMATION FOR SEQ ID NO: 7:

(i) SEQUENCE CHARACTERISTICS:
        (A) LENGTH: 18 bases
        (B) TYPE: nucleic acid
        (C) STRANDEDNESS: single
        (D) TOPOLOGY: linear
```

(iii) HYPOTHETICAL: NO (iv) ANTI-SENSE: YES (xi) SEQUENCE DESCRIPTION: SEQ ID NO: 7:

CTCCAAGTAA TCGTCAAT                                                    18

(2) INFORMATION FOR SEQ ID NO: 8:

(i) SEQUENCE CHARACTERISTICS:
            (A) LENGTH: 18 bases
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO: 8:

AGGATGCCTT TGATAGAG                                                    18

(2) INFORMATION FOR SEQ ID NO: 9:

(i) SEQUENCE CHARACTERISTICS:
            (A) LENGTH: 20 bases
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 9:

GTCTTGCCAC CTCTTCTCGG                                                  20

(2) INFORMATION FOR SEQ ID NO: 10:

(i) SEQUENCE CHARACTERISTICS:
            (A) LENGTH: 18 bases
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO: 10:

TTCCTCTTCT GCATGGAC                                                    18

(2) INFORMATION FOR SEQ ID NO: 11:

(i) SEQUENCE CHARACTERISTICS:
            (A) LENGTH: 18 bases
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO: 11:

GGGGATTTTT ATTACCAC                                                    18

(2) INFORMATION FOR SEQ ID NO: 12:

```
    (i) SEQUENCE CHARACTERISTICS:
        (A) LENGTH: 18 bases
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 12:

GATGAAAGCC ATCTAAAC                                                        18

(2) INFORMATION FOR SEQ ID NO: 13:

(i) SEQUENCE CHARACTERISTICS:
        (A) LENGTH: 20 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 13:

ACTCTTCCTT TGACATTCAT                                                      20

(2) INFORMATION FOR SEQ ID NO: 14:

(i) SEQUENCE CHARACTERISTICS:
        (A) LENGTH: 23 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 14:

AGCAGCATTG ACAGAACCAC TCT                                                  23

(2) INFORMATION FOR SEQ ID NO: 15:

(i) SEQUENCE CHARACTERISTICS:
        (A) LENGTH: 18 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 15:

ACATTCATTA TTTTCTCC                                                        18

(2) INFORMATION FOR SEQ ID NO: 16:

(i) SEQUENCE CHARACTERISTICS:
        (A) LENGTH: 57 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 16:
```

```
GGCCGCTCTG GTTATGGTCA CCTGATGAGT CCGTGAGGAC GAAACCTCTG GGCGTTT          57

(2) INFORMATION FOR SEQ ID NO: 17:

(i) SEQUENCE CHARACTERISTICS:
        (A) LENGTH: 36 bases
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 17:

CTAGAAACGC CCAGAGGTCG TGACCATAAC CAGAGC                                 36

(2) INFORMATION FOR SEQ ID NO: 18:

(i) SEQUENCE CHARACTERISTICS:
        (A) LENGTH: 57 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 18:

GGCCGCCTCA ATGTATCTTC CCTGATGAGT CCGTGAGGAC GAAACAGCAA AAACCGT          57

(2) INFORMATION FOR SEQ ID NO: 19:

(i) SEQUENCE CHARACTERISTICS:
        (A) LENGTH: 36 bases
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 19:

CTAGACGGTT TTTGCTGTCG AAGATACAT TGAGGC                                  36

(2) INFORMATION FOR SEQ ID NO: 20:

(i) SEQUENCE CHARACTERISTICS:
        (A) LENGTH: 58 bases
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 20:

GGCCGCAAAG GAACGCAGAG CTGATGAGTC CGTGAGGACG AAACCCAGCT CTATCAAT         58

(2) INFORMATION FOR SEQ ID NO: 21:

(i) SEQUENCE CHARACTERISTICS:
        (A) LENGTH: 37 bases
        (B) TYPE: nucleic acid
        (C) STRANDEDNESS: single
        (D) TOPOLOGY: linear
```

```
      (iii) HYPOTHETICAL: NO (iv) ANTI-SENSE: N0

(xi) SEQUENCE DESCRIPTION: SEQ ID NO: 21:

CTAGATTGAT AGAGCTGGGT CCTCTGCGTT CCTTTGC                              37

(2) INFORMATION FOR SEQ ID NO: 22:

(i) SEQUENCE CHARACTERISTICS:
          (A) LENGTH: 51 bases
          (B) TYPE: nucleic acid
          (C) STRANDEDNESS: single
          (D) TOPOLOGY: Linear (iii) HYPOTHETICAL: NO (iv) ANTI-SENSE: YES (xi) SEQUENCE DESCRIPTION: SEQ ID NO: 22 :

UCUGGUUAUG GUCACCUGAU GAGUCCGUGA GGACGAAACC UCUGGGCGUU U              51

(2) INFORMATION FOR SEQ ID NO: 23:

(i) SEQUENCE CHARACTERISTICS:
          (A) LENGTH: 51 bases
          (B) TYPE: nucleic acid
          (C) STRANDEDNESS: single
          (D) TOPOLOGY: linear (iii) HYPOTHETICAL: NO (iv) ANTI-SENSE: YES (xi) SEQUENCE DESCRIPTION: SEQ ID NO: 23 :

CUCAAUGUAU CUUCCCUGAU GAGUCCGUGA GGACGAAACA GCAAAAACCG U              51

(2) INFORMATION FOR SEQ ID NO: 24:

(i) SEQUENCE CHARACTERISTICS:
          (A) LENGTH: 51 bases
          (B) TYPE: nucleic acid
          (C) STRANDEDNESS: single
          (D) TOPOLOGY: linear (iii) HYPOTHETICAL: NO (iv) ANTI-SENSE: YES (xi) SEQUENCE DESCRIPTION: SEQ ID NO: 24 :

AAAGGAACGC AGAGCUGAUG AGUCCGUGAG GACGAAACCC AGCUCUAUCA A              51
```